United States Patent [19]

Gross

[11] 3,993,616

[45] Nov. 23, 1976

[54] ALKALI METAL CARBOXYLIC POLYELECTROLYTE SOLUTIONS WITH N-METHYLOL CROSSLINKER

[75] Inventor: James Richard Gross, Lake Jackson, Tex.

[73] Assignee: The Dow Chemical Company, Midland, Mich.

[22] Filed: Aug. 5, 1974

[21] Appl. No.: 494,692

[52] U.S. Cl. .................. 260/29.4 UA; 128/296; 260/33.4 R; 260/851
[51] Int. Cl.² .................. C08L 33/02; A61L 15/00
[58] Field of Search ............ 260/29.4 UA, 29.6 WB, 260/33.4 R

[56] References Cited
UNITED STATES PATENTS

| | | | |
|---|---|---|---|
| 2,557,266 | 6/1951 | Dittmar et al. | 260/29.6 WB |
| 3,245,933 | 7/1965 | Muskat | 260/29.6 HN |
| 3,514,419 | 3/1969 | Darlow et al. | 260/29.6 H |
| 3,546,142 | 12/1970 | Michaels et al. | 260/29.6 WB |
| 3,758,641 | 9/1973 | Zweigle | 260/29.6 WB |
| 3,806,485 | 4/1974 | Frisque | 260/29.6 WB |
| 3,812,070 | 5/1974 | Kelley | 260/29.4 UA |
| 3,839,254 | 10/1974 | Fang | 260/29.4 UA |
| 3,867,330 | 2/1975 | Frisque | 260/29.6 WB |

*Primary Examiner*—Murray Tillman
*Assistant Examiner*—A. H. Koeckert
*Attorney, Agent, or Firm*—Benjamin G. Colley

[57] ABSTRACT

Water swellable absorbent articles, made from polyelectrolytes, containing free carboxylic groups, together with methods for their preparation, and a composition useful to make said articles are disclosed. The composition contains N-substituted amide compounds as the crosslinking agents. The articles are crosslinked by heating and/or removing substantially all of the water from the precursor composition.

The absorbent articles are useful as surgical sponges, diapers, tampons, meat trays, bath mats and the like.

10 Claims, No Drawings

3,993,616

ALKALI METAL CARBOXYLIC POLYELECTROLYTE SOLUTIONS WITH N-METHYLOL CROSSLINKER

BACKGROUND OF THE INVENTION

This invention relates to water swellable absorbent articles made from crosslinked polyelectrolytes, methods for their preparation, and to an aqueous solution consisting of polyelectrolytes containing free carboxylic groups which is useful to make absorbent articles.

It is known from U.S. Pat. Nos. 3,669,103 (Harper, et al.) and 3,670,731 (Harmon) that cross-linked polymeric sorbents can be sandwiched between flexible supports to achieve disposable diapers or dressings.

It is further known from U.S. Pat. Nos. 2,988,539 (Cohen et al.); 3,393,168 (Johnson); 3,514,419 (Darlow et al.) and 3,557,067 (Burns et al.) that water swellable cross-linked carboxylic copolymers can be prepared. However, these prior art copolymers are all crosslinked during copolymerization or crosslinked after polymerization with subsequent neutralization of the carboxylic acid groups to form water swellable polyelectrolytes and hence these prior art polyelectrolytes cannot be crosslinked in situ as a coating on a substrate or as a flexible film thereof.

It is further known from Ser. No. 468,794, filed May 9, 1974 that carboxylic synthetic polyelectrolytes can be crosslinked after polymerizaton by the use of a nucleophilic displacement reaction using polyhaloalkanols, sulfonium zwitterions, haloepoxy alkanes, polyglycidyl ethers and mixtures thereof. The advantage of the present invention over this technique is that the crosslinking reaction proceeds by an acid catalyzed elimination reaction of the N-substituted amide crosslinker with the carboxylic polyelectrolytes to achieve crosslinked and swellable polyelectrolytes.

SUMMARY OF THE INVENTION

The present invention comprises a composition, having a pH in the range from 1.0 to 6.5 and preferably in the range from 4.0 to 6.0, which is useful to form water swellable articles of a carboxylic type synthetic polyelectrolyte which consists of a solvent such as lower alcohols, water, or mixtures thereof, about 5 to about 60 percent, preferably about 15 to about 40 percent by weight, based on the solvent, of a carboxylic polyelectrolyte, and 0.05 to 5.0% by weight, and preferably 0.2 to 0.5% by weight, based on the polyelectrolyte, of a poly N-methylol or poly N-alkoxymethyl crosslinking agent reactive with free carboxylic groups. The crosslinking agent can be monomers and polymers containing two or more N-methylol or N-alkoxymethyl groups.

The invention further comprises methods of making discrete films, absorbent articles, pariculates, fibers, and the products of these processes wherein the above solution on various substrates, is heated to a temperature greater than about 30° C. and preferably from about 90° to about 150° C. to effect the crosslinking of the polyelectrolyte and to remove excess solvent.

In order to obtain very high production rates of absorbent articles, it may be desirable to replace part or nearly all of the water in the polyelectrolyte solution with a lower alcohol such as methanol or ethanol. This substitution results in lower solution viscosities at a given percent solids and promotes rapid drying.

The final products of the present invention are thus water swellable and are useful where ever aqueous solutions need to be absorbed. Examples of the diverse utilities are surgical sponges, catamenial tampons, diapers, meat trays, paper towels, disposable door mats, disposable bath mats and disposable litter mats for household pets.

DETAILED DESCRIPTION

Examples of carboxylic synthetic polyelectrolytes useful in this invention are the ammonium or alkali metal salts of homopolymers of acrylic or methacrylic acid and copolymers with one or more ethylenically unsaturated comonomers. The only limitation being that any copolymer, to be useful in preparing highly absorbent polymer according to this invention, must be essentially water soluble in the salt form and must contain a minimum of 2 mole percent of an olefinically unsaturated carboxylic acid polymerized therein. The alternating copolymers of maleic anhydride and the maleic and fumaric acids and esters are useful when rendered water soluble by an appropriate base. One skilled in the art of radical addition copolymerization could prepare any number of suitable heteropolymers containing sufficient carboxylic functionality to render them water soluble upon neutralization and thus be useful in this invention.

Following is a list of applicable polymers which could be prepared from readily available monomers and converted to the salt form;
  acrylic acid - acrylate copolymers
  acrylic acid - acrylamide copolymers
  acrylic acid - olefin copolymers
  polyacrylic acid
  acrylic acid - vinyl aromatic copolymers
  acrylic acid - styrene sulfonic acid copolymers
  acrylic acid - vinyl ether copolymers
  acrylic acid - vinyl acetate copolymers
  acrylic acid - vinyl alcohol copolymers
  copolymers of methacrylic acid with all the above comonomers
  copolymers of maleic acid, fumaric acid and their esters with all the above comonomers
  copolymers of maleic anhydride with all the above comonomers If desired, the foregoing polyelectrolytes can also be sulfonated by treatment with $SO_3$, chlorosulfonic acid or fuming sulfuric acid in an inert organic solvent.

The crosslinking agents useful in this invention are monomers and polymers containing two or more N-methylol or N-alkoxymethyl groups.

Illustrative examples of these polymeric crosslinking agents are:
  poly(N-methylolacrylamide and poly(N-alkoxymethyl acrylamide) resins having a molecular weight range from 200 to 60,000;
  urea-formaldehyde resins having a molecular weight range from 160 to 5,000 and
  mixtures thereof.

Examples of the monomeric crosslinking agents are:
  dimethoxydihydroxy ethylene urea
  N,N-dimethylol ethyl carbamate
  tetramethylol acetylene diurea
  dimethylol urone
  dimethylol ethylene urea
  dimethylol propylene urea
  dimethylol adipic amide
  and mixtures thereof.

The crosslinking technique used in this invention to transform water soluble polyelectrolytes into insoluble but water swellable polymers can be called an acid catalyzed condensation reaction between the substituted amide group of the crosslinker and pendant carboxylic acid groups of the polyelectrolyte.

The rate of crosslinking is concentration dependent and is a factor in this invention. In solution, when the concentration of the cross-linker is very low, the rate of reaction is quite slow (pot life 10–48 hours before gelation). Once the solution is applied to a substrate surface and evaporation of solvent begins, the rate of cross-linking accelerates. Applying heat at this time increases the reaction rate even more.

If the cross-linking reaction is allowed to proceed in the original solution as by heating, aging, or excessive amounts of cross-linker, the absorbent articles of this invention cannot be fabricated. The solution will become progressively more viscous and stringy until it forms a continuous gel which could not be spread, sprayed or spun.

In the method of making water swellable films by the present invention the above solution of the polyelectrolytes is spread on a flat plate or roller of metal, plastic, or other impervious substrate and heated to a temperature greater than 30° C. to crosslink the polyelectrolyte and drive off the excess water and/or alcohol. The film is then peeled off the plate or roller by a scraper to recover the intact film for subsequent storage or use.

It is sometimes desirable to add a small amount of a surfactant to the polyelectrolyte solution to aid in flowing on and removing the continuous film from the water impervious substrate. A secondary benefit of using a surfactant is to increase the wettability of the final dry absorbent film. Either anionic or nonionic surfactants may be used. Examples of the useful surfactants are the sodium alkyl sulfonates and ethylene oxide derivatives of alkylated phenols and the like.

Similarly, when an absorbent article is prepared, the article which is to be the substrate is coated with the solution of the polyelectrolyte and then the coating is crosslinked. It is to be understood that for the purposes of this invention the coating step implies a complete coating or a discontinuous coating. Thus when a fiberous substrate such as cellulose batting, paper, woven or non-woven cloth, and the like are used as the substrate, the solution can be applied in a discontinuous manner, i.e. in a pattern of large dots, squares, or grid lines to retain the inherent flexibility of the fiberous substrate and at the same time vastly improve its water absorbency. In this instance plasticizers are not needed. Wood pulp can be coated by slurrying it in the polyelectrolyte solution followed by a fluffing operation.

If desired, the water swellable film prepared as above can be used per se as the inner absorbent layer in baby diapers. It is sometimes advantageous that the film be disintegrated into flakes, strips or powders. This is accomplished by crushing or comminuting the film in a hammer mill, blenders, or the like. If long flat strips are desired, the film can be sliced widthwise with appropriate slicers.

In some instances, water swellable fibers are desired. These can be prepared by extruding the above solution of the polyelectrolytes into a bath comprising lower alkyl ketones such as acetone, methyl ethyl ketone, diethyl ketone and the like. Alcoholic solutions may be extruded into a non-aqueous coagulant such as chlorinated hydrocarbons, i.e. methylene chloride, perchloroethylene and the like. The soft extruded fibers are then removed from the bath by any convenient means such as a three or five roll cluster and carried through a heated chamber at a temperature greater than about 30° C. and preferably in the range from about 70° to about 150° C. to dry and to crosslink the polyelectrolyte fibers.

The absorbency of the crosslinked polyelectrolytes (grams solution gelled per gram of polyelectrolyte) is determined in the following manner using synthetic urine (0.27 N sodium chloride solution).

A 0.5 gram sample of a crosslinked polyelectrolyte is weighed into a 250 ml. beaker, a 0.27 N sodium chloride solution (150 ml.) is poured into the beaker and allowed to soak for 2 hours at room temperature, with occasional stirring. The swelled polyelectrolyte is then collected by filtration and the gel capacity is reported as grams of solution gelled per gram of polymer salt.

The following examples are presented solely to illustrate but not limit the invention.

EXAMPLES 1–5

20 grams (0.0694 moles) of polyacrylic acid (Rohm & Haas Acrysol A-5) was treated with 2.08 grams (0.052 moles) of sodium hydroxide dissolved in 2.08 g. water to produce a polyelectrolyte solution of 25.4% solids which was 75 mole percent sodium acrylate with a pH of about 5. Then various amounts of substituted amide curing agents were added to the solution and the mixtures were spread on a polished chrome plate with a 25 mil draw bar to form films. After air drying, the films were stripped from the plate, cured in an oven and the absorbencies determined as set forth above. The results are set forth in Table I.

TABLE I

| Example | Curing Agent | Weight Percent (based on Polymer solids) | Curing Conditions (hours/° C) | Absorbency (gm solution gm/polymer) Absorbency |
|---------|--------------|------------------------------------------|-------------------------------|------------------------------------------------|
| 1 | 1 | 5  | 72/100  | 48 |
| 2 | 1 | 4  | 120/100 | 64 |
| 3 | 2 | 10 | 120/100 | 62 |
| 4 | 3 | 10 | 18/150  | 74 |
| 5 | 4 | 10 | 18/150  | 95 | notes:
1 - poly(N-methylolacrylamide) having a viscosity of 900 cps (Brookfield RV 100 rpm, spindle no. 6) for a 36% aqueous solution
2 - water soluble, low molecular weight urea-formaldehyde resin sold by Cyanamid under the name Cyrez 933
3 - dimethoxydihydroxy ethylene urea ethylene urea Reactant 2035, Proctor Chemical Co.
4 - N,N-dimethylol ethyl carbamate - Permfresh 227, Sun Chemical Corp.

EXAMPLE 6

A solution of poly(ethylene-co-maleic anhydride) (Monsanto EMA-31) was prepared by dissolving 12.6 grams (0.1 moles) of the polymer in water, adding 7.2 grams (0.18 moles) of sodium hydroxide and diluting to a 25% solids solution. This solution was blended with 0.222 grams (4% by weight based on the 90% neutralized EMA-31 of the poly(N-methylol acrylamide) used in Example 1 and a film was cast as set forth above. The film was cured for 22 hours at 150° C. to give an absorbency of 65 grams of 0.27 N sodium chloride solution per gram of polymer.

EXAMPLES 7–10

Eighty grams of sodium styrene sulfonate, 20 grams of acrylic acid and 300 grams of deionized water were heated to 50° C. for 18 hours to give a poly (Na styrene sulfonate-co-acrylic acid) (PSSAA) solution of 25% solids.

This solution was mixed with various amounts of poly(N-methylol acrylamide) as the curing agent or crosslinker. Films were made of the solution, cured, and tested as indicated hereinbefore. The results are set forth in Table II.

TABLE II

| Example | Curing Agent Wt. % (based on PSSAA) | Curing Conditions (hours/° C) | Absorbency (gm/gm) |
|---|---|---|---|
| 7 | 5 | 17/150 | 7.2 |
| 8 | 2 | 1.5/150 | 10.2 |
| 9 | 1 | 1.5/150 | 19.4 |
| 10 | 0.5 | 26/150 | 44 |

The lower concentration of the curing agent used in these examples compared to the preceding examples illustrates the high efficiency of poly(N-methylolacrylamide) in curing a copolymer of acrylic acid and sodium styrene sulfonate.

EXAMPLES 11–13

Three mixtures were made up having the following compositions:

| Part A | Part B | Part C |
|---|---|---|
| 600g. deionized water | 437.5g. ethyl acrylate | 175g. deionized water |
| 0.75g Triton Gr-5* | 77.2g. methacrylic acid | 2.0g. sodium bisulfite |
| 1.75g. sodium persulfate | | |

*dioctylsodium sulfosuccinate

Part A was charged to a 2 liter reactor and brought to 40° C. while under vigorous nitrogen purge. Eighteen milliliters of Part B was added to the reactor followed by all of Part C. The remainder of Part B was added over the next 2.5 hours while the temperature was held at 39°–41° C. The latex was then digested at 60° C. for 1.5 hours, cooled to 30° and bottled. The latex contained 40.6 non-volatiles.

1125 g. of the above latex was added in a small stream over a period of 25 minutes to a slowly stirred solution of 187.16 g. 50% NaOH in 547.9 g. deionized water. After the polymer had all dissolved, the viscous solution was heated at 50° C. for 22 hours to complete the saponification. The resulting solution (25.4% solids) had a Brookfield viscosity of 16,200 cps. at 25° C. (No. 5 spindle, 10 rpm). The polymer is 50% ethylacrylate by moles with the remainder being sodium acrylate and methacrylate.

An 80 gram sample of the above solution was blended with 0.25 grams of acetic acid to render the solution acidic (2% free acid by moles) then blended with various amounts of curing agents and cast on polished chromium plate with a 25 mil draw bar. After air drying, the films were lifted from the plate and placed in a 150° oven for various times. The absorbency (gel capacity) of the various films in 0.27 N. NaCl is set forth in Table III.

TABLE III

| Example | Curing Agent | Wt.% Based on Polymer | Curing Conditions hours/° C | Absorbency gm/gm |
|---|---|---|---|---|
| 11 | poly(N-methylol acrylamide) | 4 | 17/150 | 32 |
| 12 | " | 3.5 | 90/150 | 42 |
| 13 | dimethoxydihydroxyethylene urea | 10 | 26/150 | 66 |

I claim:
1. A solution having a pH from about 1.0 to about 6.5 and useful to form water swellable articles of a carboxylic synthetic polyelectrolyte which comprises
   1. a solvent consisting of water, lower alcohols, or mixtures thereof,
   2. about 5 to about 60% by weight based on the amount of solvent of an alkali metal carboxylic polyelectrolyte or mixtures thereof, and
   3. .05 to 5.0% by weight based on the polyelectrolyte of a poly N-methylol or poly N-alkoxymethyl crosslinking agent reactive with free carboxylic acid groups.

2. The solution as set forth in claim 1 wherein said crosslinking agent is selected from monomers and polymers containing two or more N-methylol or N-alkoxy methyl groups.

3. The solution as set forth in claim 1 wherein the carboxylic polyelectrolyte which is dissolved comprises 50 mole percent ethyl acrylate and the remainder being sodium acrylate and sodium methacrylate.

4. The solution as set forth in claim 2 wherein the carboxylic polyelectrolyte which is dissolved comprises 50 mole percent ethyl acrylate and the remainder being sodium acrylate and sodium methacrylate.

5. The solution as set forth in claim 3 wherein the crosslinking agent is poly(N-methylol acrylamide).

6. The solution as set forth in claim 4 wherein the crosslinking agent is poly(N-methylol acrylamide).

7. A method of preparing a water swellable polyelectrolyte which comprises the steps of
   1. preparing a solution as set forth in claim 1,
   2. evaporating about 75% of the solvent therefrom to obtain a substantially dry water-swellable polyelectrolyte.

8. A method of preparing a swellable polyelectrolyte which comprises the steps of
   1. preparing a solution as set forth in claim 2,
   2. evaporating about 75% of the solvent therefrom to obtain a substantially dry water-swellable polyelectrolyte.

9. The substantially dry water-swellable polyelectrolyte produced by the method of claim 7.

10. The substantially dry water-swellable polyelectrolyte produced by the method of claim 8.

* * * * *